(12) United States Patent
Yang et al.

(10) Patent No.: US 8,444,839 B2
(45) Date of Patent: May 21, 2013

(54) POLYMERIC SORBENT SHEETS AS ION RESERVOIRS FOR ELECTROBLOTTING

(75) Inventors: Xuemei Yang, Walnut Creek, CA (US); Cory M. Panattoni, Winters, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 0 days.

(21) Appl. No.: 13/323,314

(22) Filed: Dec. 12, 2011

(65) Prior Publication Data

US 2012/0090999 A1     Apr. 19, 2012

Related U.S. Application Data

(63) Continuation of application No. 11/955,955, filed on Dec. 13, 2007, now Pat. No. 8,075,755.

(51) Int. Cl.
*C12M 1/42* (2006.01)
(52) U.S. Cl.
USPC .......................... 204/614; 204/613; 204/464

(58) Field of Classification Search
USPC ................. 204/456, 462–464, 606, 613, 614
See application file for complete search history.

(56) References Cited

U.S. PATENT DOCUMENTS 4,840,714 A * 6/1989 Littlehales .................... 204/464
5,149,408 A * 9/1992 Perlman ........................ 530/427

* cited by examiner

*Primary Examiner* — J. Christopher Ball
(74) *Attorney, Agent, or Firm* — Kilpatrick Townsend & Stockton LLP

(57) ABSTRACT

Electroblotting for the transfer of electrophoretically separated species from a gel to a transfer membrane is performed in a semi-dry format with sheets of absorbent polyester or polyester/cellulose blend wetted with buffer solution in place of the traditional buffer-wetted filter paper. The result is effective electroblotting at a lower electric current level than that obtained with filter paper and thereby less resistance heating of the gel, the transfer membrane, and the species being transferred.

22 Claims, No Drawings

POLYMERIC SORBENT SHEETS AS ION RESERVOIRS FOR ELECTROBLOTTING

CROSS REFERENCE TO RELATED APPLICATION

This application is a continuation of co-pending U.S. patent application Ser. No. 11/955,955, filed Dec. 13, 2007, the contents of which are incorporated herein by reference.

BACKGROUND OF THE INVENTION

1. Field of the Invention

This invention resides in the field of gel electrophoresis, and relates in particular to the transfer of electrophoretically separated species from a slab gel in which the species were separated to a sheet-form support matrix in which the species can be detected, identified, and in some cases, quantified.

2. Description of the Prior Art

The electroblotting of proteins, nucleic acids, or biological species in general from an electrophoresis slab gel to a membrane of nitrocellulose, nylon, polyvinyl difluoride, or similar materials is a common means by which a biochemist can identify the components of, and otherwise characterize, essentially any biological mixture. In electroblotting, the flat surfaces of the gel and membrane are placed in full direct contact and an electric current is passed through them in a direction transverse to the gel and membrane to transfer the species in the same way that the species were mobilized within the gel when an electric current was passed in a direction parallel to the gel. When the species are DNA fragments, the transfer is termed a Southern blot after its originator, the British biologist Edwin M. Southern. By analogy, the electroblotting of RNA fragments is termed Northern blotting, and the electroblotting of proteins or polypeptides is termed Western blotting. The analytical procedures that are performed on the species in the membrane are those that are appropriate to the type of species that are transferred. For example, in Southern and Northern blotting analysis is begun by the treatment of the species on the transfer membrane with a hybridization probe followed by labeling with a fluorescent or chromogenic dye, while in Western blotting, the analysis begins with treatment of the target proteins with antibodies.

Electroblotting of either the Southern, Northern, or Western type requires electrodes on either side of the gel and membrane stack and a source of ions to carry the electric current, and is typically performed in either a wet or a semi-dry format. In wet blotting, buffer solutions placed between the electrode and the gel or membrane serve as the source of ions, while in semi-dry blotting, the buffer solutions are replaced with filter papers wetted with the buffer solution. Semi-dry blotting therefore uses a transfer stack, also referred to as a "blotting sandwich," that consists of, in order, a first sheet of buffer-wetted filter paper, the blotting membrane, the gel, and a second sheet of buffer-wetted filter paper. A "dry" electroblotting system is disclosed in an International Application published under the Patent Cooperation Treaty, Publication No. WO 2006/091525 A2, international publication date 31 Aug. 2006, entitled "Electro-blotting Devices, Systems, and Kits, and Methods for Their Use," Invitrogen Corporation, applicant. uses no liquid buffers other than those residing in the gels, The ion reservoirs in this "dry" system are anodic and cathodic gel matrices that are placed between the corresponding electrode and the transfer stack, which consists only of the electrophoresis gel and the membrane. The system is termed "dry because it uses no liquid buffers other than those residing in the gel matrices that serve as the ion reservoirs.

One of the hazards encountered in electroblotting is heat generation due to the electric current. Excessive heat generation can cause damage to the proteins or other species being transferred, or to the gel, and nonuniform heating can result in unreliable or nonuniform transfers. Heat generation can be limited by using a low current or a buffer of low ionic strength, but these can result in incomplete transfers or in an excessive amount of time for completion of the transfer.

SUMMARY OF THE INVENTION

It has now been discovered that effective electroblotting in a semi-dry format can be achieved at a low voltage and allows the use of a high current with low resistance in a relatively short period of time by substituting sheets of polyester or a polyester/cellulose blend for the filter paper of the prior art. The polyester and polyester/cellulose sheets are commonly used as wipes for sanitary or clean-room needs or for general absorbency. With these sheets, effective transfers can be achieved in approximately 35 minutes at 25V or less, and in some cases at 20V or less or even 15V or less, with low resistance and a correspondingly reduced rate of heat generation.

DETAILED DESCRIPTION OF THE INVENTION AND PREFERRED EMBODIMENTS

The polyester that is used in those embodiments of the invention that use polyester sheets can be any conventional polyester that is used for the wipes cited above. The polyester can thus be any polycondensation product of a dicarboxylic acid with a dihydroxy alcohol, that is wettable by water and is able to absorb and retain an aqueous buffer solution. Examples of the dicarboxylic acids are maleic acid, fumaric acid, phthalic acid, adipic acid, and terephthalic acid. Examples of the dihydric alcohols are ethylene glycol, diethylene glycol, propylene glycol, and dipropylene glycol. Preferred polyesters are long-chain polymers composed of at least 85% by weight of an ester of a terephthalic acid and one of the dihydric alcohols listed above. The polyester may or may not be crosslinked, although non-crosslinked polyester is preferred. Hydrophilic polyester compositions are preferred, and hydrophilicity can be imparted to hydrophobic polyesters by conventional means, such as for example treatment of the polyester with a hydrophilic composition. One such composition is an ethoxylated polyester and a surfactant. Other treatments are known to those skilled in the art. Examples of polyester fabrics suitable for use in this invention are those sold under the trademarks VWR SPEC-WIPE® (VWR International, Leicestershire, United Kingdom); ANTICON® and ANTICON®MILLISEAL® (Milliken & Company, LaGrange, Ga., USA); VECTRA® ALPHA®, ALPHAWIPE®, ALPHASORB®, ALPHA10®, and MIRACLE WIPE® (ITW-Texwipe Company, Mahwah, N.J., USA); and ULTRASEAL® and VALUSEAL™ (Berkshire Corporation, Great Barrington, Mass., USA).

The cellulose that is used in those embodiments of the invention that use polyester-cellulose sheets can be any form of cellulose, either natural or modified. Examples are wood pulp cellulose, cotton cellulose, cellulose acetate, hydroxypropyl cellulose, methyl cellulose, and carboxymethyl cellulose. Polyester-cellulose blends will preferably contain a polyester content of from about 10% to about 90% polyester by weight, most preferably from about 30% to about 70% by weight. In all cases, whether polyester or a polyester-cellulose blend, the material can be either woven or non-woven. For polyester-cellulose blends, non-woven material is preferred. Materials known in the art as "hydroentangled" polyester/cellulose blends can also be used. Examples of polyester-cellulose blends suitable for use in this invention are those sold under the trademarks DURX® and MICROFIRST® (Berkshire Corporation, Great Barrington, Mass., USA); C1 Wiper and PROZORB® (Contec, Spartanburg, S.C., USA); and TECHNI-CLOTH® (ITW-Texwipe Company, Mahwah, N.J., USA).

The dimensions of the sheets are not critical and can vary. The length and width, or lateral dimensions in general, of each sheet should be at least as great as the corresponding dimensions of the gel from which the species are to be transferred. The thickness of each sheet should be at least great enough to allow the sheet to retain enough buffer solution to allow the free transport of ions across to the sheet and to transmit sufficient electric potential to effect the transfer of the species rapidly and evenly across the lateral dimensions. The thicknesses can be the same as those of conventional filter paper. In most applications, the benefits of the invention will be achieved with sheet thicknesses of from about 0.1 cm to about 3.0 cm, and preferably from about 0.3 cm to about 1.0 cm.

The porosities of the sheets and their ability to retain an aqueous buffer solution will be similar if not identical to those of the sheets in their conventional known use as wipes for sanitary and clean-room use. Typical absorbencies for such sheets are within the range of about 200 mL/m$^2$ to about 600 mL/m$^2$.

The sheets will be wetted with buffer solution in the same manner as the filter paper of the prior art is wetted. Conventional buffer solutions, preferably aqueous, can be used. Examples of buffers are ethylenediamine tetraacetic acid (EDTA), succinate, citrate, aspartic acid, glutamic acid, maleate, cacodylate, 2-(N-morpholino)-ethanesulfonic acid (MES), N-(2-acetamido)-2-aminoethanesulfonic acid (ACES), piperazine-N,N'-2-ethanesulfonic acid (PIPES), 2-(N-morpholino)-2-hydroxy-propanesulfonic acid (MOPSO), N,N-bis-(hydroxyethyl)-2-aminoethanesulfonic acid (BES), 3-(N-morpholino)-propanesulfonic acid (MOPS), N-2-hydroxyethyl-piperazine-N-2-ethanesulfonic acid (HEPES), 3-(N-tris-(hydroxymethyl)methylamino)-2-hydroxypropanesulfonic acid (TAPSO), 3-(N,N-bis[2-hydroxyethyl]amino)-2-hydroxypropanesulfonic acid (DIPSO), N-(2-hydroxyethyl)piperazine-N'-(2-hydroxypropanesulfonic acid) (HEPPSO), 4-(2-hydroxyethyl)-1-piperazine propanesulfonic acid (EPPS)N-[tris(hydroxymethyl)-methyl]glycine (Tricine), N,N-bis(2-hydroxyethyl)glycine (Bicine), (2-hydroxy-1,1-bis(hydroxymethyl)ethyl)amino]-1-propanesulfonic acid (TAPS), N-(1,1-dimethyl-2-hydroxyethyl)-3-amino-2-hydroxypropanesulfonic acid (AMPSO), tris(hydroxy methyl)amino-methane (Tris), and bis[2-hydroxyethyl]iminotris-[hydroxymethyl]methane (BisTris). Other buffers known in the art may be used as well.

Electrophoresis gels from which the species can be transferred include any gels known to serve as media for electrophoresis. Examples are agarose gels, polyacrylamide gels, starch gels, urea gels, formamide gels, and any other denaturing or non-denaturing gels. The transfer membrane can likewise be of any material to which electrophoretically separated species can be transferred by electroblotting. Examples are nitrocellulose and other cellulose derivatives, nylon, and polyvinyl difluoride.

The operating conditions under which electroblotting is performed in accordance with this condition are analogous to those used in conventional semi-dry electroblotting. The transfer stack is prepared by placing the various wetted polyester or polyester/cellulose sheets, membrane and gel in flat surface contact in any order, and preferably immediately adjacent to each other. Thus, the transfer membrane and the gel are placed in direct contact to form the inner layers of the transfer stack, one buffer-wetted polyester or polyester/cellulose sheet is placed on the side of the gel not occupied by the membrane, and a second buffer-wetted polyester or polyester/cellulose sheet is placed on the side of the membrane not occupied by the gel. Intervening or additional sheets or layers can also be included, but are not preferred. The single wetted sheets on either side of the stack can be replaced by two or more sheets to increase the thicknesses of the outer layers, but in general a single sheet on each side will suffice.

The transfer stack, which is defined herein to be the gel, the transfer membrane, and the two buffer-wetted absorbent sheets, can be placed in direct contact with solid flat electrode plates, and a voltage is then applied between the plates and across the stack. As noted above, an advantage of the invention is that electroblotting can be performed at relatively low voltages compared to prior art electroblotting that involves the use of filter paper in place of the wetted polyester or polyester/cellulose sheets of this invention. In addition, the voltage during electroblotting remains substantially constant, i.e., with minimal if any increase in voltage during the course of the run. In preferred electroblotting transfers using the features of this invention, a voltage of from about 5 volts to about 25 volts and a current of from about 1 mA/cm$^2$ to about 2 A/cm$^2$, more preferably from about 1 mA/cm$^2$ to about 100 mA/cm$^2$, and most preferably from about 5 mA/cm$^2$ to about 20 mA/cm$^2$. The exposure time to the electric current will be that which is sufficient to achieve the full transfer of the species, and lower currents will require longer exposure times. In most cases, however, best results are obtained with exposure times of 60 minutes or less, preferably from about 3 minutes to about 50 minutes, more preferably from about 5 minutes to about 40 minutes, and most preferably from about 10 minutes to about 35 minutes.

Any species that are capable of being transferred by electroblotting can be transferred by the system or method of this invention. This includes proteins, peptides, nucleic acids, and oligonucleotides. The nucleic acids and oligonucleotides include both RNA and DNA.

The following examples are offered as illustration and are not intended to limit the scope of the invention.

EXAMPLES

A standard protein mixture sold by Bio-Rad Laboratories, Inc. of Hercules, Calif., USA, under the product name "ALL BLUE PRECISION PROTEIN STANDARDS," including three high-intensity reference bands at 25 kD, 50 kD, and 75 kD a respectively, was separated by slab gel electrophoresis on a series of identical 12.5% polyacrylamide Tris-HCl gels measuring 8.5 cm×6.7 cm with a thickness of 1 mm. Transfer stacks were prepared by stacking each gel with a nitrocellulose transfer membrane measuring 15 cm by 9.5 cm with a thickness of 0.001 cm, and two buffer-wetted absorbent sheets, one on each of the outer sides of the gel/nitrocellulose stack. The absorbent sheets, all of which were commercially available wipes of various materials, each measured 8.5 cm×6.7 cm in lateral dimensions and 0.5 cm in thickness and were thoroughly wetted with Tris-CAPS buffer solution at pH 9.6, the buffer at the anode side further containing methanol and the buffer at the cathode side further containing sodium dodecyl sulfate. Absorbent sheet materials both within and outside the scope of the invention were tested, as was extra thick filter paper (of cotton-derived cellulose) from Bio-Rad Laboratories, Inc. (Hercules, Calif., USA), the filter paper representing the prior art. The transfer stacks were placed between plate electrodes, and dc electrical currents were applied across the stacks at 120 mA (2.1 mA/cm$^2$) for 35 minutes, 240 mA (4.2 mA/cm$^2$) for 17 minutes, 360 mA (6.3 mA/cm$^2$) for 9 minutes, and in some cases 480 mA (8.4 mA/cm$^2$) for 5 minutes. In each case, the voltage were observed and recorded at both the beginning and the end of the transfer period, and the blotting quality was also observed. The blotting quality was termed "good" when the resulting blotting was clear and sharp, "OK" when the resulting blotting was clear but not sharp, and "poor" when the resulting blotting was neither clear nor sharp. The results are shown in the table below.

While the foregoing description describes various alternatives, still further alternatives will be apparent to those who are skilled in the art and are within the scope of the invention.

In the claims appended hereto, the term "a" or "an" is intended to mean "one or more." The term "comprise" and variations thereof such as "comprises" and "comprising," when preceding the recitation of a step or an element, are intended to mean that the addition of further steps or elements is optional and not excluded. All patents, patent applications, and other published reference materials cited in this specification are hereby incorporated herein by reference in their entirety. Any discrepancy between any reference material cited herein and an explicit teaching of this specification is intended to be resolved in favor of the teaching in this specification. This includes any discrepancy between an art-understood definition of a word or phrase and a definition explicitly provided in this specification of the same word or phrase.

TABLE

Experimental Results Including Comparative Data

| Absorbent Sheet ↓ Product Name | Conditions→ | 120 mA 35 min | Blotting Quality | 240 mA 17 min | Blotting Quality | 360 mA 9 min | Blotting Quality | 480 mA 5 min | Blotting Quality |
|---|---|---|---|---|---|---|---|---|---|
| Polyester: | | | | | | | | | |
| (1) VWR SPEC-WIPE ® 7 | | 13 V→11 V | good | 34 V→430 V | good | 37 V→26 V | good | | |
| (2) ANTICON ® MILLISEAL ® | | 8 V→15 V | good | 20 V→33 V | good | 31 V→38 V | good | 34 V→42 V | good |
| (3) ANTICON ® standard weight | | 10 V→9 V | good | 21 V→20 V | good | 27 V→24 V | good | 38 V→33 V | good |
| (4) ANTICON ® heavy weight | | 22 V→20 V | good | 28 V→32 V | good | 34 V→28 V | good | | |
| (5) VECTRA ® ALPHA ® 10 | | 11 V→12 V | good | 33 V→36 V | good | 48 V→32 V | good | | |
| (6) ULTRA-SEAL ® 3000 | | 14 V→16 V | good | 18 V→22 V | good | 36 V→29 V | good | 36 V→46 V | good |
| (7) VALUSEAL ® 1500 | | 8 V→10 V | good | 28 V→29 V | good | 29 V→26 V | good | 35 V→39 V | good |
| (8) ANTICON ® GOLD GOLDSORB (filament polyester) | | 11 V→13 V | good | 27 V→24 V | good | 39 V→33 V | good | | |
| (9) GAMMA-WIPE 120 (knitted non-run polyester) | | 15 V→18 V | OK | 24 V→26 V | OK | 36 V→32 V | OK | | |
| Polyester/Cellulose Blend: | | | | | | | | | |
| (10) DURX ® 770 (non-woven) | | 9 V→12 V | OK | | | | | | |
| (11) MICROFIRST ® MF (non-woven) | | 8 V→11 V | good | 12 V→15 V | good | 18 V→19 V | good | 31 V→31 V | good |
| (12) C1 (hydroentangled) | | 9 V→10 V | good | 18 V→18 V | good | 25 V→25 V | good | 33 V→36 V | good |
| (13) PROZORB ® (engineered for maximum sorbency) | | 8 V→11 V | good | 10 V→14 V | good | 16 V→18 V | good | 25 V→25 V | good |
| (14) ITW TX TECHNI-CLOTH ® | | 15 V→20 V | good | | | | | | |
| (15) DURX ® 670 | | 15 V→21 V | good | | | | | | |
| Materials Outside the Scope of This Invention: | | | | | | | | | |
| (16) polyurethane: HYDRO-SORB | | 65 V→55 V | poor | | | | | | |
| (17) cellulose: SCOTCH-BRITE ® | | 22 V→23 V | poor | | | | | | |
| (18) Filter paper | | 17 V→37 V | good | 30 V→52 V | good | 42 V→58 V | good | | |

The suppliers of products listed in the Table were as follows:
 (1): VWR International, Leicestershire, United Kingdom
 (2), (3), (4), (8): Milliken & Company, LaGrange, Ga., USA
 (5), (14): ITW-Texwipe Company, Mahwah, N.J., USA
 (6), (7), (9), (10), (11), (15): Berkshire Corporation, Great Barrington, Mass., USA
 (12), (13): Contec, Spartanburg, S.C., USA
 (16): Perfex Corporation, Poland, N.Y., USA
 (17): 3M, St. Paul, Minn., USA
 (18): Bio-Rad Laboratories, Inc., Hercules, Calif. USA The results in the Table indicate that in general, the polyester and polyester/cellulose blend materials allowed transfer of the proteins to occur at lower voltages under a given current level than either polyurethane, cellulose, and filter paper.

What is claimed is:

1. A transfer stack for transfer of electrophoretically separated species from a gel to a membrane, said transfer stack comprising:
 said gel,
 said membrane immediately adjacent to said gel and in flat surface contact therewith, and
 two sheets of absorbent material wetted with buffer solution, one said sheet immediately adjacent to said gel on the side thereof opposite the side in contact with said membrane and the other said sheet immediately adjacent to said membrane on the side thereof opposite the side in contact with said gel, each said sheet comprising a member selected from the group consisting of polyester and polyester/cellulose blends.

2. The transfer stack of claim 1 wherein each said sheet consists essentially of polyester.

3. The transfer stack of claim 1 wherein each said sheet consists essentially of a polyester/cellulose blend.

4. The transfer stack of claim 1 wherein each said sheet consists essentially of a hydroentangled polyester/cellulose blend.

5. The transfer stack of claim 1 wherein each said sheet consists essentially of a non-woven polyester/cellulose blend.

6. The transfer stack of claim 1 wherein said membrane is a member selected from the group consisting of nitrocellulose and polyvinylidene difluoride.

7. The transfer stack of claim 1 wherein said membrane is nitrocellulose.

8. The transfer stack of claim 1 wherein said gel is polyacrylamide.

9. The transfer stack of claim 1 wherein said gel is polyacrylamide and said membrane is nitrocellulose.

10. A method for transferring electrophoretically separated species from a gel to a membrane, said method comprising passing an electric current, by imposing a voltage, across a transfer stack comprising:

said gel, said membrane immediately adjacent to said gel and in flat surface contact therewith, and two sheets of absorbent material wetted with buffer solution, one said sheet immediately adjacent to said gel on the side thereof opposite the side in contact with said membrane and the other said sheet immediately adjacent to said membrane on the side thereof opposite the side in contact with said gel, each said sheet comprising a member selected from the group consisting of polyester and polyester/cellulose blends.

11. The method of claim 10 wherein said voltage is from about 5 volts to about 25 volts and said current is from about 1 mA/cm$^2$ to about 2 A/cm$^2$.

12. The method of claim 10 wherein said voltage is from about 5 volts to about 15 volts and said current is from about 1 mA/cm$^2$ to about 100 mA/cm$^2$.

13. The method of claim 10 wherein each said sheet consists essentially of polyester.

14. The method of claim 10 wherein each said sheet consists essentially of a polyester/cellulose blend.

15. The method of claim 10 wherein each said sheet consists essentially of a hydroentangled polyester/cellulose blend.

16. The method of claim 10 wherein each said sheet consists essentially of a non-woven polyester/cellulose blend.

17. The method of claim 10 wherein said membrane is a member selected from the group consisting of nitrocellulose and polyvinylidene difluoride.

18. The method of claim 10 wherein said membrane is nitrocellulose.

19. The method of claim 10 wherein said gel is polyacrylamide.

20. The method of claim 10 wherein said gel is polyacrylamide and said membrane is nitrocellulose.

21. The method of claim 10 wherein said species are members selected from the group consisting of proteins and peptides.

22. The method of claim 10 wherein said species are members selected from the group consisting of nucleic acids and oligonucleotides.

* * * * *